United States Patent
Wang

(10) Patent No.: US 8,545,822 B2
(45) Date of Patent: Oct. 1, 2013

(54) LONG WEAR TOPICAL COMPOSITION

(75) Inventor: Tianxiang Wang, Dix Hills, NY (US)

(73) Assignee: Dermaceutical Products Inc., Hauppauge, NY (US)

( * ) Notice: Subject to any disclaimer, the term of this patent is extended or adjusted under 35 U.S.C. 154(b) by 17 days.

(21) Appl. No.: 13/286,564

(22) Filed: Nov. 1, 2011

(65) Prior Publication Data

US 2012/0107254 A1     May 3, 2012

Related U.S. Application Data

(60) Provisional application No. 61/408,742, filed on Nov. 1, 2010.

(51) Int. Cl.
*A61K 8/00* (2006.01)
*A61Q 1/06* (2006.01)
*A61Q 1/10* (2006.01)

(52) U.S. Cl.
CPC .... *A61Q 1/06* (2013.01); *A61Q 1/10* (2013.01)
USPC ........... 424/64; 424/401; 424/70.6; 424/70.7; 424/63

(58) Field of Classification Search
None
See application file for complete search history.

(56) References Cited

U.S. PATENT DOCUMENTS

| | | | |
|---|---|---|---|
| 4,803,067 A | 2/1989 | Brunetta et al. | |
| 5,118,496 A | 6/1992 | Herstein | |
| 5,183,588 A | 2/1993 | Salerno et al. | |
| 5,183,589 A | 2/1993 | Brunetta et al. | |
| 6,406,683 B1 | 6/2002 | Drechsler et al. | |
| 6,482,398 B1 | 11/2002 | Rabe et al. | |
| 6,558,682 B2 | 5/2003 | Yen et al. | |
| 7,160,550 B2 | 1/2007 | Brieva et al. | |
| 2010/0152135 A1 * | 6/2010 | Blin | 514/63 |

FOREIGN PATENT DOCUMENTS

EP            998908 A2    10/2000
WO    WO 2008148809 A1 * 12/2008

OTHER PUBLICATIONS

MSDS of CAS 75009-88-0 retrieved from "http://www.lookchem.com/cas-750/75009-88-0.html" on Mar. 20, 2013 (p. 1).*
"Gelest SIB 1660.0" MSDS from Gelest (Nov. 5, 2004) pp. 1-3.*
"Catalysis" from Wikipedia (pp. 1-6) retrieved online on Jun. 11, 2013.*

* cited by examiner

*Primary Examiner* — Bethany Barham
(74) *Attorney, Agent, or Firm* — Fish & Richardson P.C.

(57) ABSTRACT

This disclosure relates to a long wear topical composition for keratinous surface. The composition includes at least one coupling agent having at least two reactive functional groups and at least one performance ingredient.

2 Claims, No Drawings

LONG WEAR TOPICAL COMPOSITION

CROSS REFERENCE TO RELATED APPLICATION

Pursuant to 35 U.S.C. §119(e), this application claims priority to U.S. Provisional Application Ser. No. 61/408,742, filed Nov. 1, 2010, the contents of which are hereby incorporated by reference.

TECHNICAL FIELD

This disclosure relates to long wear topical compositions, as well as related products and methods.

BACKGROUND

It is highly desirable for performance ingredients, such as pigments, high shine emollients, or biologically active ingredients, to stay longer on keratinous surface. To achieve this goal, the current state-of-the-arts approaches use film forming polymers to imbed the performance ingredients in the polymeric film. However, there are several major disadvantages in these approaches. Although said compositions can be effective in providing long wear and/or transfer resistance, the continuous polymeric film exerts stress on the keratinous surface. This makes the skin feels tight and uncomfortable. The films also lacks the consumer much preferred emolliency and shine. Examples of such compositions are disclosed U.S. Pat. Nos. 6,558,682; 6,482,398; 6,406,683; and 7,160,550. Another example is the popular long wear lip product under the trade name Lipfinity. This lip product has exceptional long wear; however, lip feels very tight and uncomfortable. It also lacks the emolliency and shine.

SUMMARY

The disclosure is based on the unexpected discovery that using a coupling agent to link performance ingredients on the keratinous surface can eliminate the need for a continuous polymeric film. This approach provides not only exceptional long wear properties, but also the consumer preferred emolliency and shine.

In one aspect, this disclosure features a topical composition for keratinous surface. The composition includes a) between 0.2 and 10 wt % of at least one coupling agent having at least two reactive functional groups, and b) at least one performance ingredient that is capable of reacting with the at least one coupling agent.

In another aspect, this disclosure features a topical composition for keratinous surface that includes at least one coupling agent having at least one reactive functional groups group and a performance functional group.

In still another aspect, this disclosure features a method that includes (a) applying a composition to a keratinous surface, in which the composition includes between 0.2 and 10 wt % of at least one coupling agent having at least two reactive functional groups, and at least one performance ingredient that is capable of reacting with the at least one coupling agent; and (b) reacting the at least one coupling agent with the at least one performance ingredient and the keratinous surface, thereby attaching the performance ingredient to the keratinous surface.

Embodiments can include one or more of the following optional features.

The at least one of the reactive functional groups can be a silane group. For example, the silane group can include at least a functional group —Si—$R_1R_2R_3$, in which each of $R_1$, $R_2$, and $R_3$, independently, is H, halo, $C_1$-$C_{16}$ alkyl, $C_2$-$C_{16}$ alkenyl, $C_1$-$C_{16}$ alkoxy, $C_3$-$C_{16}$ cycloalkyl, $C_3$-$C_{16}$ cycloalkenyl, $C_1$-$C_{16}$ heterocycloalkyl, $C_2$-$C_{16}$ heterocycloalkenyl, aryl, or heteroaryl, provided that at least one of $R_1$, $R_2$, and $R_3$ is $C_1$-$C_{16}$ alkoxy.

The at least one performance ingredient can include a pigment or a dye.

The at least one performance ingredient can include silicone oil. For example, the silicone oil can include polydiemthiconol, or a block copolymer between polydimethicone and polyacrylate, polyurethane, polyester, polypeptide, protein, or polyamide.

The at least one performance ingredient can include a biologically active ingredient. For example, the biologically active ingredient can include a wrinkle reduction compound, a skin whitening compound, an anti-inflammatory compound, an anti-septic compound, an anti-dandruff compound, an anti-acne compound, or a compound classified as Category I OTC drugs listed in the FDA OTC drug monograph.

The at least one performance ingredient can include at least one heteroatom X, in which X is O, S, N, Cl, or F.

The at least one performance ingredient can include at least one OH group.

The composition can further include an oil having a refractive index of at least 1.40.

The composition can further include 0.1-20 wt % (e.g., 1-10 wt %) of an alcohol.

The composition is a solid composition.

The product can be a lipstick.

The performance functional group can be a colorant moiety.

The performance functional group can include a silicone oil moiety. For example, the silicone oil moiety can include polydiemthiconol, or a block copolymer between polydimethicone and a polyacryte, polyureathane, polyester, polypeptide, protein, or polyamide.

The performance functional group can include a biologically active moiety. For example, the biologically active moiety can be derived from a wrinkle reduction compound, a skin whitening compound, an anti-inflammatory compound, an anti-septic compound, an anti-dandruff compound, an anti-acne compound, and a compound classified as Category I OTC drugs listed in the FDA OTC drug monograph.

The composition described the present disclosure can take a number of forms (e.g., solid, cream, gel, or liquid forms) often associated with a topical composition. Unless otherwise indicated, all percentages disclosed herein are by total weight of a composition.

Other features and advantages of the composition described in this disclosure will be apparent from the description and the claims.

DETAILED DESCRIPTION

The topical composition described herein includes at least one coupling agent and at least one performance ingredient.

1. Coupling Agent

The coupling agent suitable for use in the composition described in this disclosure can be a chemical compound of any types containing at least two reactive functional groups that have both organic or/and inorganic functional reactivity at ambient environment and temperature. The reactive functional group can be the organic functional group that is capable of forming a chemical bond, such as covalent, ionic or strong hydrogen bonds. A strong hydrogen bond can be a bond between a polymer in a keratinous surface or performance ingredient and one of the reactive functional groups in the coupling agent. Examples of suitable reactive functional groups include silane, aldehyde, amino, anhydride, carboxylate, phosphonate, sulfonate, epoxy, ester, halogen, hydroxyl, alkoxyl, isocynate, phosphine, phosphate, and sulfur. In some embodiments, the two reactive functional groups in the coupling agent allow one reactive function group to bind with a performance ingredient, and the other to bind to a polymer in a keratinous surface so as to affix the performance ingredient onto the keratinous surface to achieve a long lasting effect.

The coupling agent can be selected from the group of silanes or, more preferably, can be an organofunctional silane having the formula: $R-[(CH_2)_m-Si-R_1R_2R_3]_a$, in which at least two of R, $R_1$, $R_2$, and $R_3$ are reactive functional groups, m=1-30, and a=1-3. A typical R contains one of the organic functional groups selected from aldehyde, amino, anhydride, carboxylate, phosphonate, sulfonate, epoxy, ester, halogen, hydroxyl, isocynate, phosphine, phosphate, and sulfur. Each of $R_1$, $R_2$, and $R_3$, independently, is H, halo, $C_1$-$C_{16}$ alkyl, $C_2$-$C_{16}$ alkenyl, $C_1$-$C_{16}$ alkoxy, $C_3$-$C_{16}$ cycloalkyl, $C_3$-$C_{16}$ cycloalkenyl, $C_1$-$C_{16}$ heterocycloalkyl, $C_2$-$C_{16}$ heterocycloalkenyl, aryl, or heteroaryl, provided that at least one of $R_1$, $R_2$, and $R_3$ is $C_1$-$C_{16}$ alkoxy. For example, at least one of $R_1$, $R_2$, and $R_3$ can form a hydrolysable group with a silicon atom. Examples of hydrolysable group include alkoxysilane groups, acyloxysilane groups, halosilane groups, or aminosilane groups. Preferred hydrolysable groups include alkoxysilane groups (e.g., methoxysilane groups or ethoxyslane groups) of the formula $-Si-OC_nH_{2n+1}$, in which n is between 0 and 16 (e.g., between 0 and 4). In use, a hydrolysable group on a coupling agent can be hydrolyzed on a keratinous surface (e.g., skin, lip, or nail) to form a reactive silanol group, which can react with another ingredient in the topical composition (e.g., the performance ingredient that contains at least one OH group) or a polymer in the keratinous surface (e.g., a polymer containing at least one OH group).

A more preferred organofunctional silane is dipodal silane, in which a in the formula above is 2. Dipodal silanes often exhibit substantial performance improvements for reactions with the performance ingredient and/or keratinous surface at the ambient environment and temperature. In some embodiments, these dipodal silanes can form tighter networks. Dipodal silanes can also be used in the combination of other functional silanes to improve the long lasting performance on the keratinous surface.

The condensation reaction between the silanol group and an OH group can be catalyzed by a Lewis acid or base. Such a catalyst can render the condensation reaction faster in the ambient temperature. A suitable Lewis acid can be an organic acid (e.g., citric acid), a wax, or a fatty acid with high acid numbers.

Commercially available organofunctional silanes include those available from Dow Corning under the trade name of Dow Corning® brand Silanes and Silane-Based Products, Evonik Industries under the trade name of Dynasylan. Commercial example of dipodal silanes include those available from Gelest Inc., such as SIB1660.0 with the chemical name of BIS[(3-METHYLDIMETHOXYSILYL)PROPYL]-POLYPROPYLENE OXIDE, and SIB1817.0 with the chemical name of BIS(TRIETHOXYSILYL)ETHANE HEXA-ETHOXYDISILETHYLENE.

The total concentration of the coupling agent(s) in the topical composition can be between 0.2 to 10 wt % (e.g., between 0.4 to 5 wt %). A combination of different coupling agents can be used for the optimum performance.

In some embodiments, the coupling process can be done either in two steps or simultaneously. For a two-step process, the coupling agent can react with one or more performance ingredients to form a complex before the topical composition is applied to a keratinous surface. The complex can then react with a polymer in the keratinous surface to affix the performance ingredient onto the keratinous surface to achieve a long lasting effect. In some embodiments, in a simultaneous process, a coupling agent containing a hydrolysable group and the performance ingredient does not react with each other before the topical composition is applied to a keratinous surface (e.g., due to a lack of water or moisture). When the topical composition is applied to the surface, the coupling agent contacts water, which hydrolyzes the hydrolysable group. The intermediate thus formed can then react with the performance ingredient (e.g., containing a OH group) and a polymer (e.g., containing an OH group) in the keratinous surface.

In some embodiments, the performance ingredient can be affixed to a keratinous surface by forming a strong hydrogen bonding with the coupling agent, which also forms a strong hydrogen bond with a polymer in a keratinous surface. In some embodiments, the bond between the performance ingredient and the keratinous surface can be one type of chemical bond (e.g., a covalent bond) and the bond between the coupling agent and the keratinous surface can be another type of chemical bond (e.g., a strong hydrogen bond).

2. Performance Ingredients

The performance ingredients described herein generally are ingredients that deliver certain performance for the topical composition. The performance includes, but not limited to, shine, color, UV filtration, and biological functionality. Exemplary performance ingredients include, but are not limited to, pigments, dyes, and other colorants; high shine ingredients, such as oils, esters, and dimethiconol; and any suitable biologically active ingredients such as those for wrinkle reduction, skin whitening, anti-inflammatory, anti-septic, anti-dandruff, and anti-acne, and those classified as Category I OTC drugs listed in the FDA OTC drug monograph.

In some embodiments, a performance ingredient can have at least one heteroatom X, in which X can be O, S, N, Cl, or F. In some embodiments, a performance ingredient can react with the reactive functional group in the coupling agent so as to link the performance ingredient with the coupling agent.

A. Organic Pigments

A pigment preferably includes about 0.05-30% (e.g., about 0.1-25%, or about 0.5-20%) by weight of the total composition. The organic pigment is generally dispersible in a liquid carrier. Particularly preferred organic pigments include red, green, blue, yellow, violet, orange pigments, and mixtures thereof. Additional suitable pigments include "Lakes" of such pigments, which refers to salts formed between anions of organic pigments and metal cations such as calcium, aluminum, barium, or zirconium cation. Particularly preferred pigment salts are aluminum Lakes of the organic pigments. In some embodiments, formation of a metal salt of an organic pigment can convert the pigment from a water soluble pigment into a water insoluble pigment. Examples of organic pigment families that may be used herein include azo (including monoazo and diazo), fluoran, xanthene, indigoid, triphenylmethane, anthroquinone, pyrene, pyrazole, quinoline, quinoline, or salts thereof. Preferred organic pigments include D&C colors, FD&C colors, or Lakes of D&C or FD&C colors. The term "D&C" refers to drug and cosmetic colors that are approved for use in drugs and cosmetics by the FDA. The term "FD&C" means food, drug, and cosmetic colors which are approved for use in foods, drugs, and cosmetics by the FDA. Certified D&C and FD&C colors are listed in 21 CFR 74.101 et seq. and include the FD&C colors Blue 1, Blue 2, Green 3, Orange B, Citrus Red 2, Red 3, Red 4, Red 40, Yellow 5, Yellow 6, Blue 1, Blue 2; Orange B, Citrus Red 2; and the D&C colors Blue 4, Blue 9, Green 5, Green 6, Green 8, Orange 4, Orange 5, Orange 10, Orange 11, Red 6, Red 7, Red 17, Red 21, Red 22, Red 27, Red 28, Red 30, Red 31, Red 33, Red 34, Red 36, Red 39, Violet 2, Yellow 7, Yellow 8, Yellow 10, Yellow 11, Blue 4, Blue 6, Green 5, Green 6, Green 8, Orange 4, Orange 5, Orange 10, Orange 11, and so on. Suitable Lakes of D&C and FD&C colors are defined in 21 CFR 82.51. Suitable red pigments include those from the monoazo, disazo, fluoran, xanthene, or indigoid families or Lakes thereof, such as Red 4, 6, 7, 17, 21, 22, 27, 28, 30, 31, 33, 34, 36, or Red 40. Typically, the metal salts are aluminum, barium, and the like. Most preferred are aluminum Lakes of the various red pigments mentioned herein.

Suitable yellow pigments include pyrazole, monoazo, fluoran, xanthene, quinoline, or salt thereof. For example, suitable yellow pigments can be Yellow 5, 6, 7, 8, 10, or 11, as well as Lakes of such yellow pigments.

Suitable violet pigments include those from the anthroquinone family, such as Violet 2 and Lakes thereof. Examples of orange pigments include Orange 4, 5, 10, 11, or Lakes thereof.

In some embodiments, organic pigments form the main color component of the topical composition. In other words, the color of the composition is attributable primarily to the organic pigments. In some embodiments, while inorganic oxides may be incorporated into the composition, the main color of the lash tint (which is black or brown) is due to the organic pigment. In some embodiments, the lash tint is a rich dark brown or black in color, which is achieved through the use of a combination of organic pigments which are not black or brown in color. The rich deep brown or black color may be achieved by combining organic pigments or Lakes thereof in the red, green, yellow, blue, violet, and orange family. Preferably, the lash tint includes a mixture of red, green, yellow, and blue organic pigments or Lakes thereof, and is deep brown or black in color. In the most preferred embodiments, the pigments include a mixture of red, green, yellow, and blue organic pigments in which the pigments are in the form of water insoluble aluminum salts. In some embodiments, these preferred compositions may include organic pigments in non-Lake form, however, since such pigments are water soluble, when used in large amounts such non-Lake organic pigments may be incompatible with the liquid carrier. If non-Lake organic pigments are present, they are generally present at about 0.0001-3%, preferably about 0.0005-1% by weight of the total composition. In some embodiments, preferred topical compositions can be dark brown or black in color and can be free from iron oxides, particularly black iron oxide, or contain such iron oxides in less than about 5-10% by weight.

B. Inorganic Pigments

When the topical composition described herein contains an inorganic pigment, it is preferred that its amount is sufficient to accentuate the color achieved with the organic pigments in the composition but not obscure the intensity of the organic pigments. Preferred ranges include about 0.001-15% (e.g., about 0.005-10% or 0.01-8%) by weight of the total composition. Suitable inorganic pigments include iron oxides such as those in red, blue, black, green, and yellow; titanium dioxide, bismuth oxychloride, and the like.

C. Particulate Fillers

In some embodiments, it may be desirable to include one or more particulate fillers in the topical composition described herein. In such embodiments, suggested ranges are about 0.001-40% (e.g., about 0.05-35% or about 0.1-30%) by weight of the total composition. Preferably, the particulate filler has an average particle diameter of 0.02 to 100 microns (e.g., 0.5 to 100 microns). Suitable particle fillers include titanated mica, fumed silica, spherical silica, polymethylmethacrylate, micronized teflon, boron nitride, acrylate copolymers, aluminum silicate, aluminum starch octenylsuccinate, bentonite, calcium silicate, cellulose, chalk, corn starch, diatomaceous earth, fuller's earth, glyceryl starch, hectorite, hydrated silica, kaolin, magnesium aluminum silicate, magnesium trisilicate, maltodextrin, montmorillonite, microcrystalline cellulose, rice starch, silk powder, silica, talc, mica, zinc laurate, zinc myristate, zinc rosinate, alumina, attapulgite, calcium carbonate, calcium silicate, dextran, kaolin, nylon, silica silylate, sericite, soy flour, tin oxide, titanium hydroxide, trimagnesium phosphate, walnut shell powder, or mixtures thereof. The above mentioned powders can be surface treated with lecithin, amino acids, mineral oil, silicone oil or various other agents either alone or in combination, which coat the powder surface and render the particles more lipophilic in nature.

D. Dyes and Color Enhancers

Dyes suitable for use in the topical composition described herein include those disclosed in U.S. Pat. No. 7,799,096. In some embodiments, dyes include nitrophenylenediamines, nitroaminophenols, azo dyes, anthraquinones or indophenols. Preferred dyes are those known by the international names or trade names HC Yellow 2HC Yellow 4, HC Yellow 5, HC Yellow 6, HC Yellow 12, Acid Yellow 1, Acid Yellow 10, Acid Yellow 23, Acid Yellow 36, HC Orange 1, Disperse Orange 3, Acid Orange 7, HC Red 1, HC Red 3, HC Red 10, HC Red 11, HC Red 13, Acid Red 33, Acid Red 52, HC Red BN, Pigment Red 57:1, HC Blue 2, HC Blue 12, Disperse Blue 3, Acid Blue 7, Acid Green 50, HC Violet 1, Disperse Violet 1, Disperse Violet 4, Acid Violet 43, Disperse Black 9, Acid Black 1, and Acid Black 52, as well as 1,4-diamino-2-nitrobenzene, 2-amino-4-nitrophenol, 1,4-bis-(.beta.-hydroxyethyl)-amino-2-nitrobenzene, 3-nitro-4-(.beta.-hydroxyethyl)aminophenol, 2-(2'-hydroxyethyl)amino-4,6-dinitrophenol, 1-(2'-hydroxyethyl)amino-4-methyl-2-nitrobenzene, 1-amino-4-(2'-hydroxyethyl)amino-5-chloro-2-nitrobenzene, 4-amino-3-nitrophenol, 1-(2'-ureidoethyl)amino-4-nitrobenzene, 4-amino-2-nitrodiphenylamine-2'-carboxylic acid, 6-nitro-1,2,3,4-tetrahydroquinoxaline, 2-hydroxy-1,4-naphthoquinone, picramic acid and the salts thereof, 2-amino-6-chloro-4-nitrophenol, 4-ethylamino-3-nitrobenzoic acid and 2-chloro-6-ethylamino-1-hydroxy-4-nitrobenzene.

In some embodiments, the dye can be a cationic dye. Particular preference is given to: (a) cationic triphenylmethane dyes, such as Basic Blue 7, Basic Blue 26, Basic Violet 2, or Basic Violet 14; (b) aromatic systems substituted with a quaternary nitrogen group, such as Basic Yellow 57, Basic Red 76, Basic Blue 99, Basic Brown 16, or Basic Brown 17; and (c) dyes containing at least one heterocycle which includes at least one quaternary nitrogen atom, such as those mentioned in claims 6 to 11 in EP-A2-998 908.

In some embodiments, dyes are in a quantity of from about 0.01 to about 20 wt % of the topical composition.

Furthermore, the topical composition described herein may also include naturally occurring dyes, such as those contained in henna red, henna neutral, henna black, chamomile flowers, sandalwood, black tea, alder buckthorn bark, sage, logwood, madder root, catechu, lotus tree, or alkanet root.

It is not necessary for the optionally present dyes in each case to be uniform compounds. Instead, as a result of the production processes for the individual dyes, the dyeing agents contemplated herein may contain subordinate quantities of still further components, provided that these do not have a disadvantageous effect on the dyeing result or must be excluded for other, for example toxicological, reasons.

In some embodiments, to achieve further, more intense coloration, the topical composition described herein may additionally contain color enhancers. The color enhancers are preferably selected from the group consisting of piperidine, piperidine-2-carboxylic acid, piperidine-3-carboxylic acid, piperidine-4-carboxylic acid, pyridine, 2-hydroxypyridine, 3-hydroxypyridine, 4-hydroxypyridine, imidazole, 1-methylimidazole, arginine, histidine, pyrrolidine, proline, pyrrolidone, pyrrolidone-5-carboxylic acid, pyrazole, 1,2,4-triazole, piperazidine, the derivatives thereof and the physiologically acceptable salts thereof.

The above-stated color enhancers may be used in a quantity of from about 0.03 to about 10 wt % (e.g., from about 0.5 to about 5 wt %) relative to 100 g of a ready-to-use dyeing agent.

E. High Shine Oils

The high shine oil described herein refers to an oil having a refractive index great than 1.40 (e.g., greater than 1.45, greater than 1.50, greater than 1.55, or greater than 1.60) and is capable of reacting with the coupling agent. The high shine oil ranges from 0.1-70%, preferably 0.5-30%, by weight of the composition.

In some embodiments, silicones preferably have a viscosity of at least 10 centistokes (e.g., at least 20 centistokes, at least 50 centistokes, at least 100 centistokes, at least 1,000 centistokes) and at/or most about 600,000 centistokes (e.g., at most about 100,000 centistokes, at most about 50,000 centistokes, or at most about 10,000 centistokes) at 25° C.

The high shine oil can include esters of the formula RCO—OR' in which each of R and R', independently, is a $C_{1-25}$, preferably a $C_{4-20}$ straight or branched chain alkyl, alkenyl or alkoxycarbonylalkyl or alkylcarbonyloxyalkyl. Examples of such esters include isotridecyl isononanoate, PEG-4 diheptanoate, isostearyl neopentanoate, tridecyl neopentanoate, cetyl octanoate, cetyl palmitate, cetyl ricinoleate, cetyl stearate, cetyl myristate, coco-dicaprylate/caprate, decyl isostearate, isodecyl oleate, isodecyl neopentanoate, isohexyl neopentanoate, octyl palmitate, dioctyl malate, tridecyl octanoate, myristyl myristate, octododecanol, and fatty alcohols such as oleyl alcohol, isocetyl alcohol, and the like, as well as the esters disclosed on pages 24-26 of the C.T.F.A. Cosmetic Ingredient Handbook, First Edition, 1988.

The high shine oil can also include glyceryl esters of fatty acids, or triglycerides, such as castor oil, lanolin oil, triisocetyl citrate, $C_{10-18}$ triglycerides, caprylic/capric/triglycerides, coconut oil, corn oil, cottonseed oil, linseed oil, mink oil, olive oil, palm oil, illipe butter, rapeseed oil, soybean oil, sunflower seed oil, walnut oil, and the like.

Additional suitable examples of the high shine oil include glyceryl esters (excluding fats and oils which are glyceryl esters of fatty acids) that are primarily fatty acid mono-di- and triglycerides modified by reaction with other alcohols. Examples of such a high shine oil include acetylated castor oil, glyceryl stearate, glyceryl dioleate, glyceryl distearate, glyceryl trioctanoate, glyceryl distearate, glyceryl linoleate, glyceryl myristate, glyceryl isostearate, PEG castor oils, PEG glyceryl oleates, PEG glyceryl stearates, PEG glyceryl tallowates, and so on.

Also suitable as the high shine oil are various lanolin derivatives such as acetylated lanolin, acetylated lanolin alcohol, and so on.

High shine non-fluorinated silicones are also suitable as the high shine oil. Suitable silicones include amodimethicone, bisphenylhexamethicone, dimethicone, dimethicone copolyol, dimethiconol, hexadecyl methicone, hexamethyldisiloxane, methicone, phenyl trimethicone, simethicone, dimethylhydrogensiloxane, stearoxy dimethicone, stearoxytrimethylsilane, vinyldimethicone, and mixtures thereof. Such silicones are available from Dow Corning as the 3225C formulation aid, Dow 190 and 193 fluids, or similar products marketed by Goldschmidt under the tradename ABIL.

Also suitable as the high shine oil are various fluorinated oils such as fluorinated silicones or perfluoropolyethers. Particularly suitable are fluorosilicones such as trimethylsilyl endcapped fluorosilicone oil, polytrifluoropropylmethylsiloxanes, and similar silicones such as those disclosed in U.S. Pat. No. 5,118,496. The high shine oil can also include mixtures of fluorosilicones and dimethylpolysiloxanes. The high shine oil can also include perfluoropolyethers such as those disclosed in U.S. Pat. Nos. 5,183,589, 4,803,067, and 5,183,588. These perfluoropolyethers are commercially available from Montefluos under the trademark Fomblin.

Other suitable high shine oils include sorbitan derivatives such as PEG sorbitan beeswax, PEG sorbitan isostearate, PEG sorbitan lanolate, PEG sorbitan laurate, PEG sorbitan oleate, PEG sorbitan palmitate, PEG sorbitan stearate, polysorbates, sorbitan trioleates, sorbitan sesquioleates, sorbitan stearates, sorbitan tristearates, and so on.

F. Biologically Active Ingredients

Biologically active ingredients suitable for the composition described in this disclosure are those that can react with coupling agent. In some embodiments, the biologically active ingredients are effective in wrinkle reduction, skin whitening, anti-inflammentary, anti-septic, anti-dandruff, and anti-acne. In some embodiments, the biologically active ingredients include those classified as Category I OTC drugs listed in the FDA OTC drug monograph.

3. Other Ingredients

The topical composition described herein can also include one or more polymers. As used herein, the term "polymer" refers a compound having at least two repeating units (each unit being derived from a compound known as a monomer). For example, the polymer can include at least three (e.g., five, ten, 20, 50, 100, or 500) repeating units and can be either a homopolymer or a copolymer.

The polymers described herein include natural, synthetic, organic, inorganic, and organic/inorganic hybrid polymers. In some embodiments, the polymers can have at least one heteroatom X, in which X can be O, S, N, Cl, or F. In some embodiments, a polymer suitable for the topical composition described herein can react with the reactive functional group in the coupling agent so as to link the polymer with the coupling agent.

A synthetic polymer can be selected from polyurethanes; polyurethane-acrylics; polyureas; polyurea-polyurethanes; polyester-polyurethanes; polyether-polyurethanes; polyesters; polyamide, polyester amides; acrylic polyesters; polyvinylpyrrolidone-based polymers; acrylic and/or vinyl polymers; polyacrylamides; silicone polymers containing acrylic parts; silicone resins; polyurea/polyurethane silicones; copolymers based on silicone resin and dimethiconol; fluoropolymers; polyquaternium polymers, and chemically modified celluloses.

Commercially available acrylic polymers include an alkyl acrylate/cycloalkyl acrylate copolymer sold by Phoenix Chem. under the name GIOVAREZ AC-5099 ML, and an acrylate/C 12-22 alkyl methacrylate copolymer sold by Rohm & Haas under the name SOLTEX OPT. Examples of vinyl polymers include vinylpyrrolidone copolymers, such as copolymers of a C2-C30 alkene (e.g., C3-C22 alkene) and combinations thereof. Examples of polyamide polymers that may be used in the disclosure include polyamide-1, polyamide-2, polyamide-3, polyamide-4 sold by Arizona Chemical under the trade name of SYLVACLEAR. Examples of vinylpyrroolidone (VP) copolymers that may be used in the disclosure include VP/vinyl laurate copolymers, VP/vinyl stearate copolymers, butylated polyvinylpyrrolidone (PVP) copolymers, VP/hexadecene copolymers sold by ISP under the name GANEX V216, VP/eicosene copolymers sold by ISP under the name GANEX V220, VP/triacontenes copolymers, or VP/acrylic acid/lauryl methacrylate copolymers. Examples of copolymers whose CTFA names (4th edition, 1991) are octylacrylamide/acrylates/butyl-aminoethyl methacrylate copolymers include the products sold under the name AMPHOMER or LOVOCRYL by National Starch. Examples of the copolymers whose CTFA names are acrylates/octylacrylamide copolymer include the products sold under the name DERMACRYL LT or DERMACRYL 79 by National Starch. Examples of polyquaternium include the products sold under the trade name of UCARE by Dow Chemical. Examples of polyurethanes whose CTFA names (4th edition, 1991) are Polyurethane-1 to Polyurethane-45, Polyurethane-24/Methyl Methacrylate Crosspolymer and Styrene/Acrylates Copolymer/Polyurethane include the products sold under the trade name of LUVISET by BASF Co. Organofunctional groups (e.g., alkoxysilane groups) in the coupling agent described above can form strong hydrogen bonds with these polymers.

Natural polymers suitable for the topical composition described herein include those selected from the group consisting of starch, cellulose, polysaccharide, proteins, keratin, rosin, and shellac. Commercially available examples of natural polymers include *Zea Mays* (Corn) Starch sold by Company Corn Products International under the trade name Farmal CS 3757, cellulose sold by Nippon Paper Chemicals Co., Ltd. under the trade name of KC Flock, carrageenan sold by the FMC under the trade name of Gelcarin, chitosan sold by Cognis Corporation under the trade name of Hydagen DCMF, hydrolyzed Keratin sold by Kemira/Maybrook under the trade name of Kera-Tein, silk, soy, and milk protein. Nature polymers typically contain hydroxyl group that can react with organofunctional groups (e.g., alkoxysilane groups) in the coupling agent described above. From 0.01 to 50% of natural polymers can be used in the topic composition described herein depending on the type of application. For example, 0.01% of whey protein is known to increase the collagen synthesis and its efficacy will be greatly enhanced by using the coupling agent to immobilize it onto the keratinous surface.

In some embodiments, the topical composition described herein can omit the polymer mentioned above. In such embodiments, the coupling agent in the topical composition can couple the performance ingredient directly to the substrate that itself is a polymer. For example, keratinous surfaces, which include skin, hair, and nail surface, are made of natural polymers that are rich in hydroxyl group. The coupling agent described herein (e.g., a silane) can directly couple the performance ingredients to the skin, hair or nail. The performance ingredients, thus, can stay on keratinous surfaces for a longer time.

The topical composition described in this disclosure can further include at least one agent commonly used in drugs, cosmetics, personal care products. For example, the agent can be demulcents, sequestrants, perfumes, oils, wax (e.g., polyethylene wax or candelilla wax), silicones, thickeners, vitamins, proteins, ceramides, plasticizers, coalescing agents, cohesion agents, alkalinizing agents, acidifying agents, emulsifies, surfactants, emollients, and preservatives.

In some embodiments, when the coupling agent includes alkoxysilane (e.g., ethoxysilane) as a hydrolysable group, the topical composition can include an alcohol (e.g., ethanol) that forms the alkoxy. Without wishing to be bound by theory, it is believed that including such an alcohol can significantly reduce the rate of hydrolysation of the hydrolysable group when the topical composition is stored in a package such that the topical composition has a long shelf life. In such embodiments, when the topical composition is applied to a keratinous surface, the rate of the hydrolysation reaction can significantly increase as the alcohol is evaporated so that the coupling reaction between the coupling agent and the performance ingredient and the coupling reaction between the coupling agent and the polymer in the keratinous surface can occur. The alcohol can be 0.1-20 wt % (e.g., 1-10 wt %) of the topical composition.

Of course, persons skilled in the art would be careful to select at least one of these optional additional compounds, and the amount of any of these optional additional compounds, such that the advantageous properties of the topical composition described herein are not substantially impaired by the addition envisaged. In particular, any additional ingredient(s) that can enhance the reactivity of the coupling agents and/or long lasting staying capability of performance ingredients on keratinous surface is preferred. Examples of such ingredients include Lewis acid and base; transitional metal ions; volatile solvent to enhance the kinetics of the reaction, manipulation of partition coefficient and/or compatibility of two solvents.

The topical composition described in this disclosure can be prepared according to the customary methods in the fields considered.

The topical composition described herein can be used in a product, such as a cosmetic product. Examples of suitable cosmetic products include lipstick, lip balm, lip gloss, hair conditioner, and hair dye. Other cosmetic products include skin care cream and lotions; color cosmetics (such as mascara, liquid, hot pour and powder foundations, makeup pencils, eye and lip liner, nail lacquer); liquid bondages; antibacterial liquid, lotion, ointments; and anti-inflammation lotions and ointments.

Unless otherwise indicated, all numbers expressing quantities of ingredients, properties such as molecular weight, reaction conditions, and so forth used in the specification and claims are to be understood as being modified in all instances by the term "about". Accordingly, unless indicated to the contrary, the numerical parameters set forth in the following specification and attached claims are approximations that may vary depending upon the desired properties sought to be obtained by the present invention. At the very least, and not as an attempt to limit the application of the doctrine of equivalents to the scope of the claims, each numerical parameter should at least be construed in light of the number of reported significant digits and by applying ordinary rounding techniques.

Any numerical value inherently contains certain errors necessarily resulting from the standard deviation found in their respective testing measurements.

The contents of all publications cited herein (e.g., patents, patent application publications, and articles) are hereby incorporated by reference in their entirety.

EXAMPLES

The following examples are illustrative and not intended to be limiting.

Example 1

Long Wear Lipstick

A topical composition for a long wear lipstick is prepared according to the following table.

| Sequence (Seq) | Ingredients | wt % |
|---|---|---|
| 1 | Polyethylene wax | 8 |
| 1 | Candelilla wax | 3 |
| 1 | Squalane | 8 |
| 1 | Diglyceryl triisostearate | 15 |
| 1 | Macademia nut oil fatty acid ester | 2.5 |
| 1 | Glyceryl tri-2-ethylhexanoate | 1.5 |
| 1 | Fine particle barium sulfate | 5 |
| 2 | BIS[(3-METHYLDIMETHOXYSILYL)PROPYL]-POLYPROPYLENE OXIDE | 2 |
| 2 | Castor oil | 10 |
| 2 | Citric acid | 0.2 |
| 2 | Pigment | 5 |
| 2 | Camphor | 0.05 |
| 3 | MQ resin | 2 |
| 3 | Dimethiconol | 15 |
| 3 | Decamethyl cyclopenta siloxane | Qs |

To make the above composition, the ingredients for Seq 2 are first mixed and grinded together with a roller mill, ball mill, or similar pigment grinding device. The ingredients in Seq 3 are mixed to form a homogeneous solution. The ingredients for Seq1 are then added to a main kettle at 95° C. When Seq 1 forms a clear solution, Seq 2 is added to the main kettle while mixing. After the temperature is lowered to 75° C., Seq 3 is added to the kettle. The kettle is maintained at 75° C. until the entire bulk is uniform for pouring. In this example and the examples below, BIS[(3-METHYLDIMETHOXYSILYL)PROPYL]-POLYPROPYLENE OXIDE is a coupling agent and is available from Gelest, Inc. under the trade name SIB 1660.0. Pigment and castor oil are performance ingredients.

Example 2

High Shine and Long Wear Lipstick

A topical composition for a high shine and long wear lipstick is prepared according to the following table.

| Sequence (Seq) | Ingredients | wt % |
|---|---|---|
| 1 | Ethylcellulose and Octyldodecanol and Hydrogenated Dilinoleyl Alcohol | Qs |
| 2 | Polyvinylstearyl Ether | 1.00 |
| 2 | Hydrogenated Myristyl Olive Oil Esters | 2.00 |
| 2 | Polyethylene | 8.00 |
| 2 | Polyethylene | 3.00 |
| 3 | *Euterpe Oleracea* Sterols and Linolenic Acid and Linoleic Acid and Oleic Acid | 5.00 |
| 3 | Castor Isostearate Succinate and Hydrogenated Castor Oil | 4.00 |
| 3 | Polybutene | 3.50 |
| 3 | Trimethylolpropane Tricaprylate/Tricaprate and Sucrose Acetate Isobutyrate | 4.00 |
| 3 | Perfluorononyl Dimethicone | 2.00 |
| 3 | Propylene Glycol Dibenzoate | 9.00 |
| 3 | Phenylisopropyl Dimethicone | 4.00 |
| 3 | PPG-26 Dimer Dilinoleate Copolymer and Isononyl Isononanoate and Ethylhexyl Isononanoate | 2.50 |
| 3 | Pentaerythrityl Tetraisostearate | 4.50 |
| 3 | Tocopheryl Acetate | 0.10 |
| 4 | BIS[(3-METHYLDIMETHOXYSILYL)PROPYL]-POLYPROPYLENE OXIDE | 2 |
| 4 | Octyldodecanol | 8.75 |
| 4 | Polyglyceryl-4 Isostearate and Cetyl PEG/PPG-10/1 Dimethicone and Hexyl Laurate | 3.75 |
| 4 | Titanium Dioxide and Triethoxycaprylylsilane | 6.13 |
| 4 | Iron Oxides and Triethoxycaprylylsilane | 0.25 |
| 4 | Iron Oxides and Triethoxycaprylylsilane | 1.75 |
| 4 | Red 7 Lake and Triethoxycaprylylsilane | 2.63 |
| 4 | Iron Oxides and Triethoxycaprylylsilane | 1.75 |
| 5 | Caprylyl Methicone | 5.40 |

To make the above composition, the ingredients for Seq 4 are first mixed and grinded together with a roller mill, ball mill, or similar pigment grinding device. The ingredients in Seqs 1 and 2 are added to a main kettle and then heated to 95° C. When Seqs 1&2 form a clear solution, the ingredients in Seq 3, 4, and 5 are added to the kettle. The temperature of the kettle is maintained at 85° C. until the entire bulk is uniform for pouring. In this example, BIS[(3-METHYLDIMETHOXYSILYL)-PROPYL]POLYPROPYLENE OXIDE is a coupling agent. Ingredients in Seq 4 except the coupling agent are performance ingredients.

Example 3

Long Wear Lip Gloss with UV Protection

A topical composition for a long wear lip gloss with UV protection is prepared according to the following table.

| Sequence (Seq) | Ingredients | wt % |
|---|---|---|
| 1 | Octyldodecanol | Qs |
| 1 | Neopentyl Glycol Diheptanoate | 14.00 |
| 1 | Ethyl Cellulose | 8.00 |
| 1 | Dextrin Palmitate | 0.50 |
| 1 | Triethylamine | 0.1 |
| 2 | Ethylhexyl Salicylate | 5.00 |
| 2 | Ethylhexyl Methoxycinnamate | 7.50 |
| 2 | Homosalate | 10.00 |
| 2 | Octocrylene | 2.79 |
| 2 | Butyl Methoxydibenzoylmethane | 3.00 |
| 2 | Tocpherol Acetate | 0.50 |
| 2 | Linoleic Acid | 0.20 |
| 2 | Hydrogenated Dilinoleyl Alcohol | 0.95 |
| 3 | 3-AMINOPROPYLTRIMETHOXYSILANE | 2 |
| 3 | Octyldodecanol | 4 |
| 3 | Polyglyceryl-4 Isostearate and Cetyl PEG/PPG-10/1 Dimethicone and Hexyl Laurate | 1 |
| 3 | Titanium Dioxide | 2 |
| 3 | Iron Oxides | 05 |
| 3 | Iron Oxides | .5 |
| 3 | Red 7 Lake | .6 |
| 3 | Iron Oxides | .5 |
| 3 | SD Alcohol | 2 |
| 3 | Caprylyl Methicone | 5.40 |

To make the above composition, the ingredients for Seq 2 are first mixed and grinded together with a roller mill, ball mill, or similar pigment grinding device. The ingredients for Seq 3 are mixed to form a homogeneous solution. The ingredients for Seq1 are then added to a main kettle at 65° C. When Seq 1 forms a clear solution, Seq 2 is added to the kettle while mixing. After the temperature is then lowered to 65° C., Seq 3 is added to the kettle. The temperature of the kettle is maintained at 65° C. until the entire bulk is uniform for pouring. In this example, 3-AMINOPROPYLTRI-METHOXY-SILANE is a coupling agent and is available from Gelest Inc. under the trade name SIA0611.0. Ingredients in Seq 3 except the coupling agent are performance ingredients.

Example 4

Long Lasting High Shine Hair Conditioner

A topical composition for a long lasting high shine hair conditioner is prepared according to the following table.

| Sequence (Seq) | Ingredients | wt % |
| --- | --- | --- |
| 1 | Dimethiconol | 7 |
| 1 | 2-HYDROXY-4-(3-METHYLDIETHOXYSILYLPROPOXY)DIPHENYLKETONE | 2 |
| 1 | Water | 0.2 |
| 2 | Dimethicone | 58.6 |
| 2 | Cyclopentasiloxane | 23.5 |
| 2 | C12-15 Alkyl Benzoate | 3 |
| 3 | SD Alcohol | 5 |
| 3 | Ethyl Ester of Hydrolyzed Silk | 0.1 |
| 4 | Phenoxyethanol | 0.2 |

To make the above composition, the ingredients for Seq 1 are first mixed and heated to 60° C. to allow limited reaction between the coupling agent (i.e., 2-HYDROXY-4-(3-METH-YLDIETHOXYSILYLPROPDXY)DIPHENYLKETONE) and dimethiconol. The remaining ingredients are then added to the batch. In this example, 2-HYDROXY-4-(3-METH-YLDIETHOXYSILYLPROPDXY)DIPHENYL-KETONE is the coupling agent and is available from Gelest under the trade name SIH6198.0, and Dimethiconol is the performance ingredient.

Example 5

Long Lasting Non-Oxidative Hair Dye

A topical composition for a long lasting non-oxidative hair dye is prepared according to the following table.

| Sequence (Seq) | Ingredients | wt % |
| --- | --- | --- |
| 1 | Water | Qs |
| 1 | EDTA | 0.1 |
| 1 | Benzophenone-3 | 0.005 |
| 1 | Phenoxyethanol | 0.5 |
| 1 | D&C Orange #4 | 0.12 |
| 1 | Ext. D&C Violet #2 | 0.014 |
| 1 | FD & C Yellow #6 | 0.018 |
| 1 | Laureth-23 | 1 |
| 1 | Carbomer 940 | 0.6 |
| 1 | Trisoproanolamine | 1.1 |
| 1 | PVP | 2.5 |
| 1 | PPG-10 Methyl Glucose Ether | 1 |
| 1 | Dimethicone Copolyol | 1.5 |
| 2 | SD Alcohol | 10 |
| 2 | 3-aminopropylsilane hydrolysate | 2 |

To make the above composition, the ingredients for Seq 1 are added to a kettle with mixing until a clear solution is formed at 50° C. After the temperature is cooled to 30° C., the ingredients for Seq 2 are added to the kettle to form the composition. In this example, 3-aminopropylsilane hydrolysate is a coupling agent and is available from Evonik under the trade name of Dynasylan® HYDROSIL 1151, and D&C Orange #4, Ext. D&C Violet #2, FD & C Yellow #6 are performance ingredients.

Example 6

Long Wear Lipstick

A long wear lipstick was prepared according to the following table.

| Seq | INCI | % |
| --- | --- | --- |
| 1 | Isododecane and Lecithin and Titanium Dioxide and Iron Oxides (C.I. 77492) and Iron Oxides (C.I. 77491) and Red 6 Lake and Red 7 Lake (CI 15850) | 14.50 |
| 1 | Isododecane | 2.40 |
| 1 | PVP/Hexadecene Copolymer | 5.50 |
| 1 | Polybutene | 9.40 |
| 2 | Hydrogenated Polydecene and Quaternium-90 Bentonite and Propylene Carbonate | 10.00 |
| 3 | Euphorbia Cerifera (Candelilla) Wax | 7.20 |
| 3 | Hydrogenated Polycyclopentadiene | 8.00 |
| 3 | Beeswax | 2.30 |
| 3 | Mica and Titanium Dioxide | 2.00 |
| 3 | Calcium Sodium Borosilicate and Titanium Dioxide and Tin Oxide | 1.00 |
| 3 | Succinic Anhydride Terminated Polydimethylsiloxane | 2.00 |
| 4 | Dimethicone | 35.50 |
| 4 | 3-(Triethoxysilyl)Propyl-Succinic Anhydride 95% | 0.20 |

To prepare the above example, the ingredients for Seq 1 were added to a beaker with propeller agitation. When a uniform solution was formed, the ingredient for Seq 2 was slowly added to the beaker under propeller agitation. When a uniform solution was formed again, the beaker was heated to 85-87° C. under propeller agitation. After the temperature of 85-87° C. was reached, the ingredients in Seq 3 were added to the above solution one by one under propeller agitation. When a uniform solution was formed, a premixed mixture of ingredients for Seq 4 was slowly added to the beaker under propeller agitation. When a uniform solution was formed again, the solution was poured into a lipstick mold at 85-87° C. and cooled quickly to form a lipstick.

What is claimed is:

1. A topical composition for keratinous surface, comprising between 0.2 and 10 wt % bis[(3-methyldimethoxysilyl)propyl]-polypropylene oxide, polyethylene wax, candelilla wax, squalane, diglyceryl triisostearate, a macadamia nut oil fatty acid ester, glyceryl tri-2-ethylhexanoate, barium sulfate, castor oil, citric acid, a pigment, camphor, MQ resin, dimethiconol, and decamethylcyclopentasiloxane.

2. A topical composition for keratinous surface, comprising between 0.2 and 10 wt % of bis[(3-methyldimethoxysilyl)propyl]-polypropylene oxide, wherein the composition comprises ethylcellulose, octyldodecanol, hydrogenated dilinoleyl alcohol, polyvinylstearyl ether, a hydrogenated myristyl olive oil ester, polyethylene, an euterpe oleracea sterol, linolenic acid, oleic acid, castor isostearate succinate, hydrogenated castor oil, polybutene, trimethylolpropane tricaprylate, trimethylolpropane tricaprate, sucrose acetate isobutyrate, perfluorononyl dimethicone, propylene glycol dibenzoate, phenylisopropyl dimethicone, a PPG-26 dimer dilinoleate copolymer, isononyl isononanoate, ethylhexyl isononanoate, pentaerythrityl tetraisostearate, tocopheryl acetate, octyldodecanol, polyglyceryl-4 isostearate, cetyl PEG/PPG-10/1 dimethicone, hexyl laurate, titanium dioxide, triethoxycaprylylsilane, iron oxide, red 7 lake, and caprylyl methicone.

* * * * *

UNITED STATES PATENT AND TRADEMARK OFFICE
CERTIFICATE OF CORRECTION

PATENT NO. : 8,545,822 B2
APPLICATION NO. : 13/286564
DATED : October 1, 2013
INVENTOR(S) : Tianxiang Wang It is certified that error appears in the above-identified patent and that said Letters Patent is hereby corrected as shown below:

In the Specification:

In column 11, Line 15, delete "Macademia" and insert -- Macadamia --, therefor.

In the Claims:

In Column 14, Line 52, in Claim 1, delete "macademia" and insert -- macadamia --, therefor.

In Column 15, Lines 58-59, in Claim 2, delete "wherein the composition comprises ethylcellulose," and insert -- ethylcellulose, --, therefor.

Signed and Sealed this
Third Day of December, 2013

Margaret A. Focarino
*Commissioner for Patents of the United States Patent and Trademark Office*